(12) United States Patent
Matusch

(10) Patent No.: US 9,599,220 B2
(45) Date of Patent: Mar. 21, 2017

(54) CYLINDER-PISTON UNIT WITH SHORT CANNULA

(71) Applicant: Rudolf Matusch, Marburg (DE)

(72) Inventor: Rudolf Matusch, Marburg (DE)

(73) Assignee: LTS LOHMANN THERAPIE-SYSTEME AG, Andernach (DE)

( * ) Notice: Subject to any disclaimer, the term of this patent is extended or adjusted under 35 U.S.C. 154(b) by 332 days.

(21) Appl. No.: 14/276,249

(22) Filed: May 13, 2014

(65) Prior Publication Data

US 2014/0245882 A1    Sep. 4, 2014

Related U.S. Application Data

(63) Continuation-in-part of application No. PCT/EP2012/072821, filed on Nov. 16, 2012.

(30) Foreign Application Priority Data

Nov. 16, 2011    (DE) .................. 10 2011 119 203

(51) Int. Cl.
   *A61M 5/46*    (2006.01)
   *F16J 1/00*    (2006.01)

(52) U.S. Cl.
   CPC .............. *F16J 1/005* (2013.01); *A61M 5/46* (2013.01)

(58) Field of Classification Search
   CPC .. A61M 5/46; A61M 5/20; A61M 2005/2006; A61M 2005/208; A61M 5/315;
   (Continued)

(56) References Cited

U.S. PATENT DOCUMENTS 6,213,977 B1    4/2001    Hjertman
6,890,319 B1 *  5/2005    Crocker ............... A01K 11/005
                                                    604/131

(Continued)

FOREIGN PATENT DOCUMENTS

DE    WO 85/00524    2/1985
DE    693 36 594 T3    5/2010
DE    698 36 594 T3    5/2010

OTHER PUBLICATIONS

DIN 13097-4, Hypodermic Needles—Part 4—Point geometry, requirements and testing. Aug. 2009.*

(Continued)

*Primary Examiner* — Nathan R Price
*Assistant Examiner* — Melissa A Snyder
(74) *Attorney, Agent, or Firm* — R. S. Lombard

(57) ABSTRACT

A cylinder-piston unit, with at least one cylinder accommodating an injection solution and having an outlet opening, and with at least one piston. The cylinder, or a component mounted upstream of the cylinder, has an end face from which, during correct emptying of the cylinder-piston unit, a short cannula protrudes, which has an outlet opening at its free end. The outlet opening has a surface with a border which has a point near the bottom or an edge near the bottom. The point near the bottom or the edge near the bottom lies 0.15-0.3 mm away from the end face or the front-most point or edge thereof. A cylinder-piston unit is developed which is intended for a disposable injector and which is suitable for virtually painless penetration of the human skin, among other reasons for the administration of highly viscous injection solutions.

5 Claims, 4 Drawing Sheets

(58) Field of Classification Search
CPC ...... A61M 2005/31521; A61M 5/31531; F16J 9/00; F16J 1/005
See application file for complete search history.

(56) References Cited

U.S. PATENT DOCUMENTS

| | | |
|---|---|---|
| 9,220,850 B2 * | 12/2015 | Kawamoto ......... A61M 5/3287 |
| 2002/0193740 A1 | 12/2002 | Alchas et al. |
| 2003/0014006 A1 | 1/2003 | Alexandre et al. |
| 2007/0021716 A1 | 1/2007 | Hansen |
| 2008/0287885 A1 | 11/2008 | Hoffmann et al. |
| 2009/0099510 A1 | 4/2009 | Poulsen |
| 2009/0227942 A1 | 9/2009 | Stroem Hansen et al. |
| 2011/0166520 A1 * | 7/2011 | Iwase ...................... A61M 5/46 604/117 |
| 2011/0214777 A1 | 9/2011 | Matusch |
| 2011/0270217 A1 | 11/2011 | Stroem Hansen et al. |
| 2012/0046615 A1 * | 2/2012 | Koiwai ............... A61M 5/3243 604/192 |

OTHER PUBLICATIONS

Essay in the "Journal of Investigative Dermatology" (2006), vol. 126, pp. 1080 to 1087, Entitled "Precise Microinjection Into Skin Using Hollow Microneedles" by Ping M. Wang, et al.

* cited by examiner

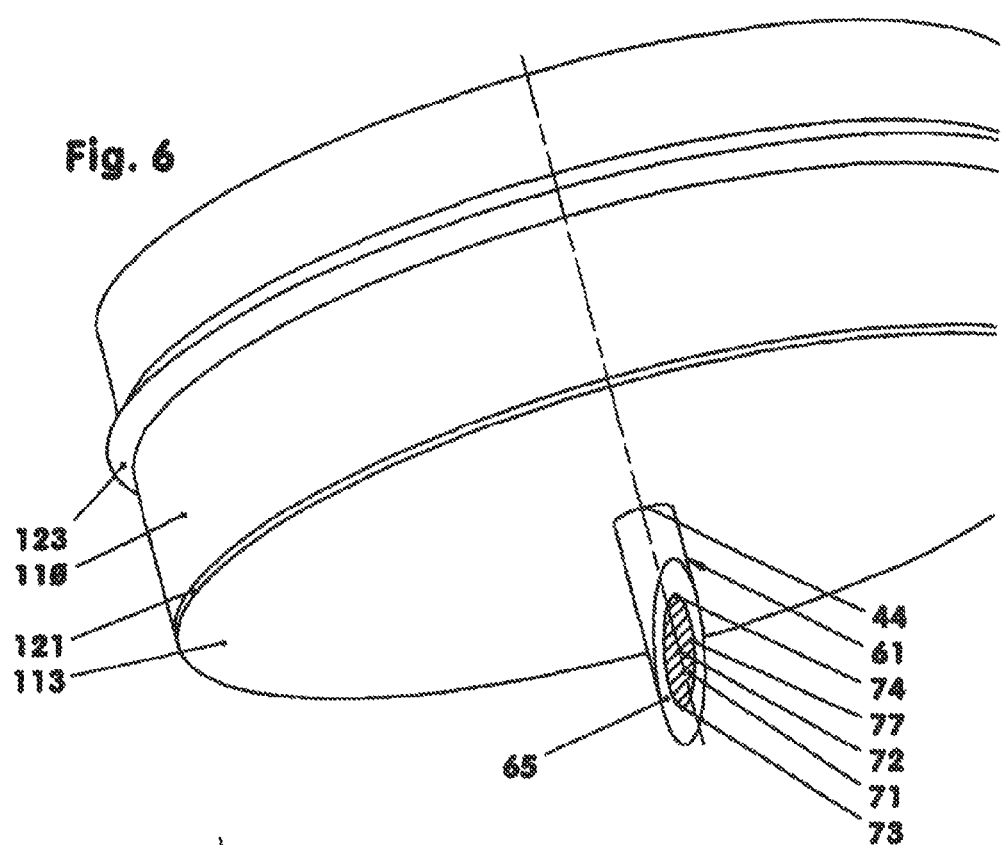
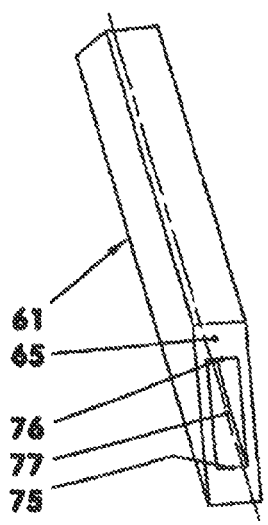
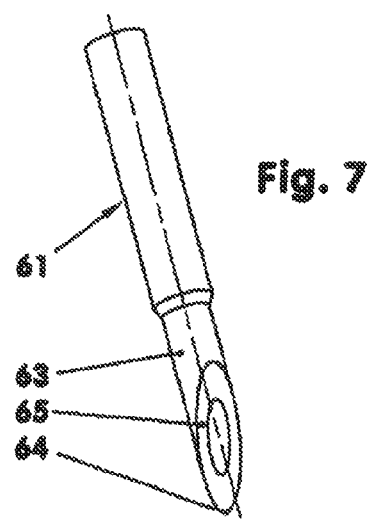

CYLINDER-PISTON UNIT WITH SHORT CANNULA

CROSS-REFERENCE TO RELATED APPLICATION

This is a continuation-in-part application of pending international application PCT/EP2012/072821 filed Nov. 16, 2012 and claiming the priority of German Application No. 10 2011 119 203 filed Nov. 16, 2011 which is hereby incorporated herein by reference in its entirety as though fully set forth.

BACKGROUND OF THE INVENTION

The invention relates to a cylinder-piston unit of a needle-free injector, with at least one cylinder accommodating an injection solution and having an outlet opening, and with at least one piston.

From an essay which appeared in the "Journal of Investigative Dermatology" (2006), volume 126 under the title "Precise Microinjection into Skin Using Hollow Microneedles" by Ping M. Wang et al., it is known to place a group of several very small hollow glass needles onto the skin of a patient who is to be inoculated, and to press them against the skin such that the glass needles, upon dispensing a liquid active substance, introduce the latter into the upper layers of skin. Since the short glass needles only have extremely thin channels, only a small amount of active substance can be dispensed, and the latter also has to have an extraordinarily low viscosity.

The object of the present invention is therefore to develop a cylinder-piston unit which is intended for a disposable injector and which is suitable for virtually painless penetration of the human skin, among other reasons for the administration of highly viscous injection solutions.

SUMMARY OF THE INVENTION

This object is achieved by the features of the main claim. The cylinder, or a component mounted upstream of the cylinder, has an end face from which, during correct emptying of the cylinder-piston unit, a short cannula protrudes, which has an outlet opening at its free end. The outlet opening has a surface with a border which has a point near the bottom or an edge near the bottom. The point near the bottom or the edge near the bottom lies 0.15-0.3 mm away from the end face or the front-most point or edge thereof.

Here, the cylinder-piston unit of a disposable injector, for example, is proposed by the invention. The disposable injector not only accommodates the cylinder-piston unit but also a drive mechanism that is installed in an injector housing and that acts on a piston-actuating ram. As possible drive mechanisms, it is possible to use spring accumulators, gas drives with openable gas cartridges, or pyrotechnic drives. Known spring energy accumulators use pretensioned mechanical or pneumatic springs or spring systems. If a spring energy accumulator is used as drive mechanism, the piston-actuating ram is held with a form fit, via at least one support rod or draw hook arranged on or in the injector housing, in order to pretension and hold this spring energy accumulator. The one or more support rods or draw hooks are retained in their locked position by means of one or more trigger elements until the use of the disposable injector. To trigger the injector, the one or more support rods or draw hooks are released, such that the piston-actuating ram, under the effect of the spring energy accumulator, can move at least approximately parallel to the centre line of the disposable injector, with the result that the injection solution present in the cylinder of the cylinder-piston unit is expelled via at least one short cannula.

According to the invention, a short cannula protrudes from the end face of the cylinder of the cylinder-piston unit and, after the injector has been placed onto the skin of the patient, penetrates only a few tenths of a millimeter into the skin of the patient during the subsequent administration of the injection solution. The depth of penetration is limited mechanically by the front end face of the injector.

With the aid of the short cannula, it is possible to administer, among other things, highly viscous protein solutions, e.g. monoclonal antibodies, without difficulty and in a virtually painless manner.

The front end face of the injector can also be the front end face of an elastomer or adhesive disc which closes the short cannula during storage of the injector and which is mounted on the cylinder so as to be displaceable in the direction of the longitudinal extent of the injector.

BRIEF DESCRIPTION OF THE DRAWINGS

Further details of the invention will become clear from the dependent claims and from the following descriptions of schematically depicted illustrative embodiments.

FIG. 6 shows a perspective view of the short cannula protruding from the elastomer disc;

FIG. 7 shows a perspective view of a short cannula with a tapered tip;

FIG. 8 shows a perspective view of a short cannula with a square cross section.

DETAILED DESCRIPTION OF THE PARTICULAR EMBODIMENTS

Figure 1:
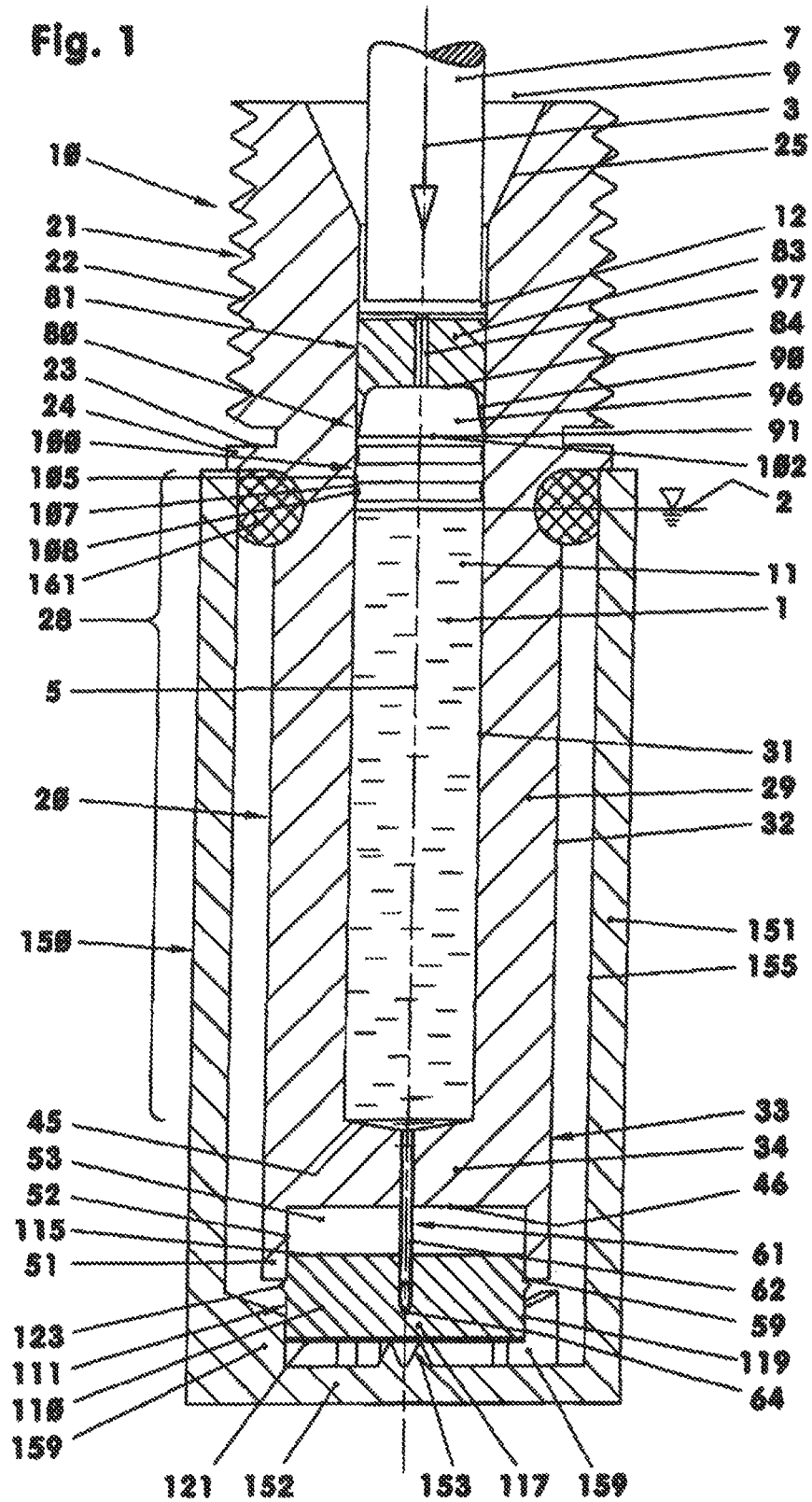
FIG. 1 shows a cylinder-piston unit with short cannula and protective housing.

FIG. 1 shows a cylinder-piston unit (10) of a disposable injector. The cylinder-piston unit (10) is composed of a cylinder (20) and a piston, for example a two-part piston (80). The cylinder (20), which at its front end carries a short cannula (61) sealed off and protected by an adhesive disc (110), is additionally surrounded, for example, by a protective housing (150). Above the piston (80), the lower part of a piston-actuating ram (7) is shown, which belongs to the disposable injector (not depicted here). The cylinder (20) is secured on the injector by means of its outer thread (22), present in the rear area of the cylinder, or by means of slits (23). In the area of the cylinder bottom, an adhesive disc (110) is also arranged between the cylinder (20) and the protective housing (150).

The for example one-part cylinder (20) is composed of a housing adapter (21), a tube portion (28) and a bottom portion (33). With the housing adapter (21), the cylinder (20) is fixed in an injector housing (not depicted). For this purpose, its radial outer wall has an outer thread (22) and at least two slits (23) lying opposite each other. The slits (23)

have a depth of 2 mm, for example. They are located at the thread end in immediate proximity to the tube portion (28). The width of the slits (23) is 0.6 mm, for example.

Between the slits (23) and the tube portion (28), there is an abutment web (24), of which the external diameter can be identical, for example, to the outer diameter of the thread. The external diameter of the tube portion (28) is more than twice as great as the diameter of the inner wall (31).

The housing adapter (21) is adjoined by the cylinder wall (29) of the tube portion (28). Along the length of the tube portion, the cylinder wall (29) has, for example, a constant wall thickness of 3.25 mm.

The bottom portion (33) comprises an outwardly plane bottom plate (34), which corresponds to the mean wall thickness of the cylinder wall (29) in the area of the tube portion (28). An annular web (51), e.g. in the shape of a cylindrical tube, is integrally formed in the outer area of the bottom plate (34). The annular web (51), which encloses a receiving space (53) for the adhesive disc, is, for example, as high as the wall thickness of the bottom plate (34). The height is 3 mm, for example. The wall thickness of the annular web (51) is about one third of the wall thickness of the cylinder wall (29) of the tube portion (28).

The inner wall (31) of the cylinder is shaped cylindrically, at least in the tube portion (28). It there has an internal diameter of 5.5 mm, for example. In the area of the housing adapter (21), the inner wall (31) of the cylinder widens out in the shape of a truncated cone. The cone angle of this widening (25) is 50 degrees, for example. The length of the widening (25) corresponds to about one third of the length of the housing adapter (21).

In the area of the bottom portion (33), the inner wall (31) of the cylinder ends in a cylinder bottom (45), of which the cone angle measures 160 degrees, for example. A short cannula (61) is arranged in the centre of the bottom portion (33). Its centre line is, for example, congruent to the centre line (5) of the cylinder-piston unit (10). In the bottom portion (33), the short cannula (61) extends for example between the cylinder bottom (45) and the plane end face (46). For assembly, it is either already placed in the injection mould during the injection-moulding of the cylinder (20) or is subsequently pressed or adhesively bonded into the finished cylinder (20).

The short cannula (61) is, for example, a thin-walled tube (62) which, for example, is produced from a stainless steel. It has an external diameter of 0.5 mm, for example. The wall thickness is generally 0.05 mm, 0.06 mm or 0.07 mm, cf. DIN 13097-4, Annex A, edition of August 2009 ("DIN" is the German acronym for the German Institute for Standardization). At its free front end, the cannula (62) has, among other things, a single cut, a facet cut or a relief cut. The respective main cutting angle is between 9 and 18 degrees, cf. DIN 13097-4, Annex B, edition of August 2009. In the present case, a main cutting angle of 18 degrees (cf. FIG. 1) or an even greater angle is preferred, since with an increasing angle the maximum length of the opening cross section becomes smaller. According to FIGS. 2 and 3, the angle measures 45 degrees Depending on the wall thickness and elasticity of the adhesive disc (110) used, the cannula tip (64) protrudes by 1 to 1.5 mm, for example, beyond the annular web (51).

According to FIG. 1, an adhesive disc (110) is arranged between the short cannula (61) and the annular web (51), in the front area of the receiving space (53) for an adhesive disc. It has a material thickness that is at least 0.4 mm greater than the depth of the receiving space (53) for the adhesive disc. According to FIG. 1, the adhesive disc (110) is placed onto the short cannula (61) such that the latter does not penetrate the front third of the adhesive disc (110). In this way, a sealing area (117) that closes the short cannula (61) from the front lies in front of the tip (64).

The substantially cylindrical outer wall of the adhesive disc (110) is guided on the cylindrical inner wall (52) of the annular web (51). According to FIG. 1, the adhesive disc (110) has, in the upper area of its outer wall, a circumferential web (123) which protrudes radially, e.g. by 0.5 mm, and via which the adhesive disc bears elastically on the front inside edge (59) of the annular web (51).

For positioning the adhesive disc (110) on the annular web (51) of the bottom portion (33), the latter can also have a radially inwardly protruding web, which is integrally formed in the front area of the annular web (51) and which protrudes elastically into a corresponding annular groove of the adhesive disc (110).

The adhesive disc (110) is made of rubber, for example, or of another elastomer and is provided, on its plane front end face, with an adhesive layer (121) composed, for example, of a pressure-sensitive adhesive. The rest of the surface areas have good sliding ability, since the adhesive disc (110) is at least partially treated with silicone oil or coated with Teflon. The pressure-sensitive adhesive of the adhesive disc (110) is such that its adhesion force with respect to the adhesive disc (110) is at least 50% greater than with respect to a disinfected skin surface (201).

If appropriate, the adhesive disc (110) has at least one lateral notch, which is oriented parallel to the centre line (5) and by means of which, upon insertion of the adhesive disc (110) into the receiving space (53), the air present therein can be easily displaced. The air can also escape via a bore arranged in the annular web (51), in proximity to the end face (46) of the bottom portion (33).

Figure 2:
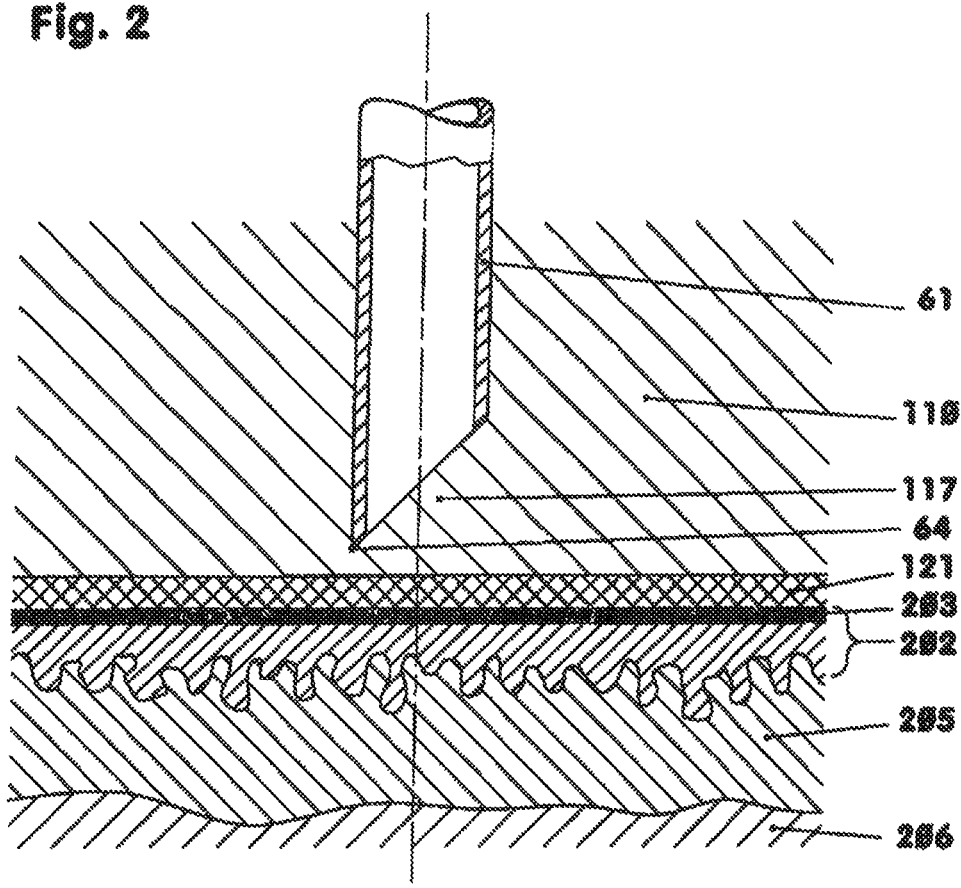
FIG. 2 shows a cross section of the short cannula after placement onto the patient's skin and before complete piercing of the elastomer disc.
Figure 3:
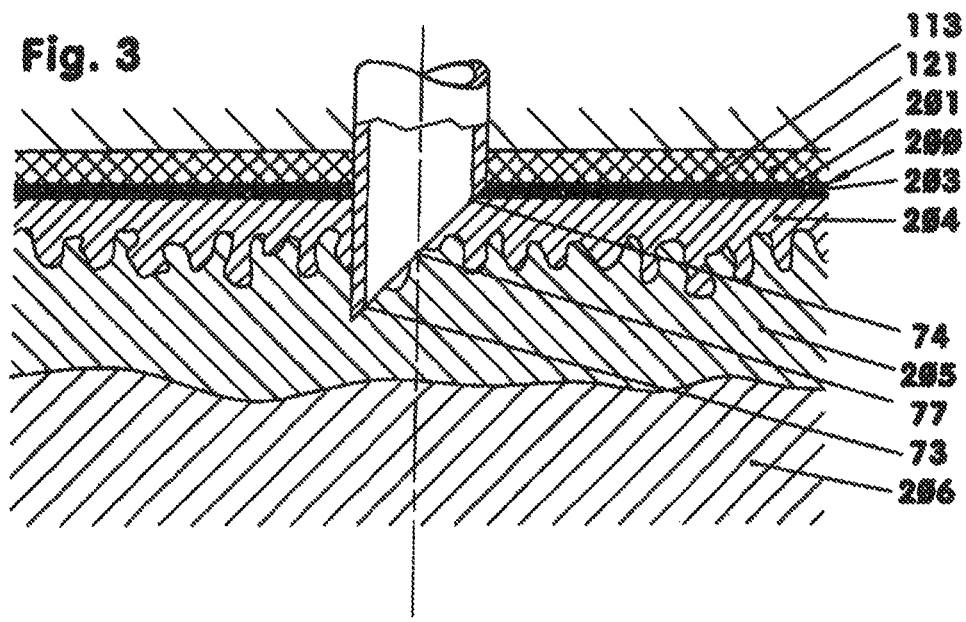
FIG. 3 shows the same as FIG. 2, but after complete piercing of the elastomer disc.

FIGS. 2 and 3 show a short cannula (61) which, with an external diameter of 0.5 mm, has a wall thickness of 0.05 mm and comprises a single cut with a cutting angle of 45 degrees, for example. According to FIG. 2, the needle tip (64) is still inserted in the adhesive disc (110) while the injector is being pressed onto the skin (200) of the patient.

According to FIG. 3, the short cannula (61) has reached its application position. As a result of the adhesive disc (110) bearing on the skin surface (201), the short cannula (61) has penetrated so deeply that its outlet opening (71) (cf. also FIG. 6) opens out into the upper area of the dermis (205). In the case of the single cut, the outlet opening (71) has an elliptical border (72). The rearmost point (74) of this border (72) situated near the bottom has passed the horny layer (203). According to FIG. 3, the front-most point (73) is positioned in the dermis (205). The area centroid (77) of the surface (71) enclosed by the border (72) lies, merely by way of example, at the transition from the epidermis (202) to the dermis (205). In this way, the point (74) near the bottom is arranged at a distance of 0.15-0.3 mm from the end face (113) of the adhesive disc (110).

If the short cannula (61) is used in a cylinder-piston unit (10) using neither an adhesive disc (110) nor an annular web (51), the short cannula (61) protrudes from the front end face of the cylinder. If this end face is curved or has a shape like a conical jacket, the distance (0.15-0.3 mm) is related, not to a plane surface (113), but instead to the edge that corresponds to the intersection curve of short cannula (61) and cylinder end face.

If, instead of a short cannula (61) with a circular cross section, a short cannula with a rectangular or square cross section is used (cf. FIG. 8), the front point (73) and the rear point (74) are replaced by an edge (76) near the bottom and a front edge (75).

FIG. 7 shows a short cannula (61) whose front end has a cannula taper (63) just in front of the cut (65) or before the outlet opening (71). In the area of the taper (63), the diameter is, for example, 0.1 mm smaller than in the rear needle area. The front needle portion, generated by material compression for example, has a minimum length in the range of half to twice the needle diameter.

According to FIG. 1, a pot-shaped protective housing (150), a sterile closure, surrounds the tube portion (28) and the bottom portion (33) with the inserted adhesive disc (110) of the cylinder (20). It consists here of a tubular jacket (151) and a plane bottom (152). In the illustrative embodiments shown, the protective housing (150), on account of its shape, is made from the plastic cyclo-olefin copolymer (COO), for example. This material has a particularly low permeability to gas and vapour. With a simpler shape, the protective housing (150) can be made of glass.

In the area of the tube portion (28), the distance between the outer wall (32) of the tube portion (28) and the inner wall (155) of the protective housing (150) is 1.5 mm, for example. The axial distance between the bottom (152) of the protective housing (150) and the adhesive disc (110) measures 1 mm, for example, according to FIG. 1.

The protective housing (150) is fixed releasably on the cylinder (20) at two locations. The first location lies at the transition between the tube portion (28) and the abutment web (24) of the cylinder (20). There, according to FIG. 1, an O-ring (161) sits in a notch of the cylinder (20) and seals the protective housing (150) in relation to the cylinder (20). At the same time, the O-ring (161) centres the protective housing (150) on the cylinder (20). Instead of a conventional O-ring (161), it is also possible to use a quad ring, a profiled ring or the like.

Upon assembly, the sealing ring (161) is clamped between the protective housing (150) and the cylinder (20), such that, in addition to the sealing function, it can also easily perform a centering and holding function. If appropriate, the sealing ring (161) can also be replaced by a tough sealing adhesive.

The second location for supporting the protective housing (150) on the cylinder (20) is situated in the bottom (152) of the protective housing (150). For radial support, the protective housing (150) has, for example, five radially oriented supporting ribs (159). These supporting ribs (159), distributed equidistantly on the circumference of the jacket (151), are, for example, integrally formed on the bottom (152) and on the jacket (151). The supporting ribs (159) have radial inner faces via which they bear on the cylindrical outer face (119) of the adhesive disc (110).

For axial support of the adhesive disc (110), the bottom (152) is additionally provided with an annular supporting web (153), which bears with its upper circular edge on the adhesive disc (110), in the central region of the latter. The edge is so narrow that it develops only a slight adhesion force with respect to the adhesive disc (110).

According to FIG. 1, the cylinder (20) is filled with an injection solution (1). The liquid level (2) of the injection solution (1) is situated in the transition area between the housing adapter (21) and the tube portion (28). A disc-shaped sealing body (100) is placed on the liquid level (2) in a sterile manner and without bubbles and, under the effect of radial clamping, bears sealingly on the inner wall (31) of the cylinder. A pot-shaped drive body (81) is arranged behind the sealing body (100). The drive body (81) bears partially on the sealing body (100) or is at a distance of, for example, 0.2 to 0.5 mm therefrom.

The sealing body (100) here is a disc whose undeformed diameter is, for example, twice as great as its disc thickness. On its circumference, the disc (100) has, for example, a grooved profile (107) with, for example, two grooves (108). The grooved profile (107) is, for example, configured such that the sealing body (100) has, in cross section, a wave line with two wave valleys forming the grooves (108). The wave line is composed here of arcs of a circle.

Figure 4:
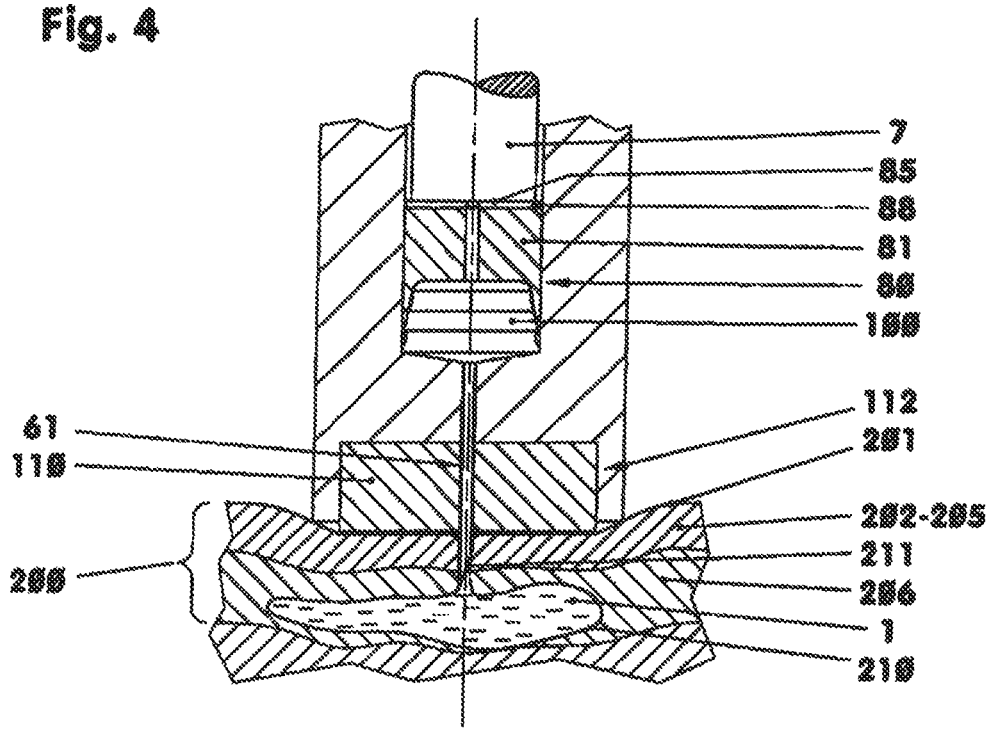
FIG. 4 shows the same as FIG. 2, but after complete piercing of the elastomer disc.

Since the sealing body (100) is an elastomer body, the wave crests of the fitted sealing disc are flattened off (cf. FIGS. 1 and 4).

The pot-shaped drive body (81), whose length corresponds to its external diameter for example, is composed of a disc-shaped impact plate (83) and of a skirt (90) formed integrally thereon. The thickness of the impact plate (83) is here slightly greater than the length of the skirt (90) (cf. FIG. 1).

The impact plate (83), which is impacted by the piston-actuating ram (7) when the injector is triggered, has at least a for example central bore (97), by which the cylinder chamber areas (11, 12) located in front of and behind the drive body (81) are connected to each other with minimal restriction. According to the illustrative embodiments, the bore (97), of which the minimum diameter is between 1 and 2 mm, ends on the rear face (85) of the drive body (81), e.g. in a channel intersection (88) composed of two channels intersecting in the area of the bore (97). The channels of the channel intersection (88) each have a semicircular cross section, wherein the diameter of the cross sections corresponds, for example, to the diameter of the bore.

The front face (84) of the impact plate (83) is adjoined by the skirt (90), which is designed as an elastic sealing lip. Starting from the front face (84), the wall of the skirt (90) tapers towards the front outer sealing edge (91), which bears elastically on the inner wall (31) of the cylinder in each operating state of the injector. In the installed state, the skirt (90) and the front face (84) enclose an immersion space (96). The latter has substantially the shape of a truncated cone, of which the cone angle measures 20 degrees, for example.

The combination of the drive body (81) and of the sealing body (100), which combination constitutes the piston (80), permits simple bubble-free filling and sterile closure of the cylinder-piston unit (10) in connection with an ejection procedure upon release of the injector, which withstands a very high compression pulse of up to $350*10^5$ Pa (pascals).

When the injector is ready for the injection, the protective housing (150) is pulled off from the cylinder (20), e.g. by manual force. In doing this, the adhesive disc (110) remains in the bottom portion (33) of the cylinder (20). The sealing ring (161) also remains on the outer wall (32) of the cylinder (20).

To be able to administer the injection solution, the injector, with the adhesive disc (110) towards the front, is placed onto the skin surface (201) of the patient. The adhesive disc (110), which is still located in its installation position (111), thus attaches itself via its adhesive layer (121) to the skin surface (201).

By the pressing force of the injector, the adhesive disc (110) is loaded in such a way that, with the locking action of the circumferential web (123) being overcome and the adhesive disc (110) being pierced, it slips along the short cannula (61) in the direction of the bottom portion (33), such that it bears with its rear end face (115) on the end face (46) of the bottom portion (33). The adhesive disc (110) is now located in its application position (112). It now completely fills the receiving space (53) for the adhesive disc. At the front, it protrudes, e.g. by 0.5 mm, beyond the annular web (51). During the pressing procedure, the increase in the pressure has the effect that, on the one hand, the adherence between the adhesive layer (121) and the skin of the patient is strengthened, and, on the other hand, the short cannula (61) protrudes by a few tenths of a millimeter out of the adhesive disc (110) (cf. FIGS. 3 and 4) in order to penetrate the skin (200).

At the same time, the injector is triggered by being pressed onto the skin (200). The piston-actuating ram (7), pretensioned by means of a mechanical or pneumatic spring for example, applies a sudden load to the two-part piston (80) in order to introduce the injection solution (1) through the short cannula into the upper layers of the skin (200) of the patient (cf. FIG. 4).

Figure 5:
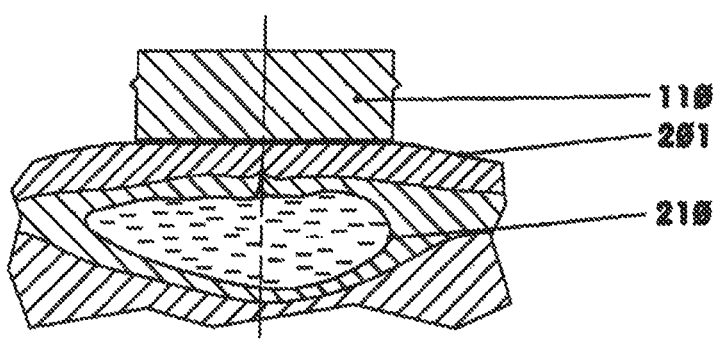
FIG. 5 shows a cross section through the elastomer disc affixed to the skin after the injector has been removed.

The generated inflow channel (211), which is formed by the jet of liquid shooting out of the short cannula (61), generally ends only in the subcutis (206). In the connective tissue of the subcutis (206), which is permeated by capillary vessels and is rich in adipose tissue, a pool (210) of injection solution then forms (cf. FIG. 5), which is fed by the liquid jet.

At least most of this pressurized pool (210) of injection solution will immediately empty via the inflow channel (211) when the injector with all its parts is lifted away from the skin (200). In the present case, after the injector has been taken away, the adhesive disc (110) remains in place because of its adhesive layer (121), until it is separately removed at a later point.

The opening initially made in the elastomer body (110) by the short cannula (61) immediately closes after the injector has been taken away. The patient removes the adhesive disc (110), including the adhesive layer (121) adhering thereto, only when the injection-induced bulging of the skin (200) has substantially receded. This is the case when the injection solution (1) has flowed off into the tissue surrounding the pool (210) of injection solution.

LIST OF REFERENCE SIGNS

1 Injection solution
2 Liquid level
3 Arrow direction upon injector release
5 Centre line
7 Piston-actuating ram
9 Environment
10 Cylinder-piston unit
11 Cylinder chamber area in front of the piston
12 Cylinder chamber area behind the piston
20 Cylinder
21 Housing adapter
22 Outer thread
23 Annular groove
24 Abutment web
25 Widening on the inside
28 Tube portion
29 Cylinder wall
31 Inner wall, radial
32 Outer wall, radial
33 Bottom portion
34 Bottom plate
44 Edge on (46)
45 Cylinder bottom, inner side of the cylinder bottom
46 End face of the bottom portion, front
51 Annular web
52 Inner wall, cylindrical
53 Receiving space for adhesive disc
59 Front edge
61 Short cannula, very short needle
62 Cannula tube
63 Cannula taper
64 Cannula tip
65 Cut, single cut
71 Outlet opening, outlet surface
72 Edge of the outlet surface, border
73 Point, front
74 Point, rear, near bottom
75 Front edge
76 Rear edge, near bottom
77 Centre of gravity of the outlet surface
80 Piston, combination of (81) and (100)
81 Drive body; body, pot-shaped
83 Impact plate
84 Front face
85 Rear face
88 Channel intersection
90 Elastic skirt; sealing lip
91 Sealing edge, edge
94 Flattening, notch
96 Immersion space, hollow space
97 Recess, bore, central
100 Sealing body, sealing disc
102 Rear face
105 Outer wall, profiled
107 Grooved profile
108 Groove
110 Adhesive disc, elastomer disc
111 Installation position
112 Application position
113 Front end face; plane end face
115 Rear end face
117 Sealing area
119 Outer face, radial
121 Adhesive layer, front, pressure-sensitive adhesive, adhesive coating
123 Circumferential web
150 Protective housing, glass; outer shell; sterile closure
151 Jacket, tubular
152 Bottom, plane
153 Supporting web, inside
155 Inner wall
159 Supporting ribs
161 O-ring
200 Skin
201 Skin surface
202 Epidermis
203 Horny layer (stratum corneum)
204 Keratinization and regeneration layer
205 Papillary and reticular layer (dermis)
206 Subcutis
210 Pool of injection solution
211 Inflow channel

What is claimed is:

1. Cylinder-piston unit (10), with at least one cylinder (20) accommodating an injection solution (1) and having an outlet opening (71), and with at least one piston (80), a piston actuating rain (7) actuating the at least one piston (80), the improvement which comprises:
the cylinder (20) has a bottom portion (33), on which a short cannula (61) is arranged congruent to the centre line (5) of the cylinder-piston unit (10), the bottom portion (33) of the cylinder (20) has a front end face (46), an elastomer adhesive disc (110), which is displaceable in the direction of a center line (5) of the cylinder-piston unit (10) between and an installation position (111) and an application position (112) is slidably arranged on the short cannula (61) and/or on the bottom portion (33), the bottom portion (33) has an annular web (51), which extends forward in a continuation of the outer wall (32) of the cylinder (20), the annular web (51) encloses a receiving space (53) for the elastomer disc (110), the elastomer disc (110) slidable within the receiving space (53), the elastomer disc (110) in the installation position (111) occupying a front area of the receiving space (53) and the short cannula (61) penetrating a predetermined portion of the elastomer disc (110), but not fully through the elastomer disc (110), in the application position (112) the elastomer disc (110) fully occupying the receiving space (53), the elastomer disc (110) in the application position (112) bearing on the front end face (46) of the bottom portion (33) and simultaneously protruding a predetermined distance beyond the annular web (51), the elastomer disc (110) having an end face (113) mounted upstream of the cylinder (20), from which, during correct emptying of the cylinder-piston unit (10) in the application position (112), the short cannula (61) protrudes, the short cannula (61) has an outlet opening (71) at its free end, the short cannula (61) in fluid communication with the cylinder (20);

the outlet opening (71) has a surface with a border (72) which has a point (74) near the bottom or an edge (76) near the bottom, and the point (74) near the bottom or the edge (76) near the bottom lies 0.15-0.3 mm away from the end face (113) of the elastomer disc (110) or the front-most point or edge (44) thereof.

2. Cylinder-piston unit according to claim 1, wherein a through-flow cross section of the short cannula (61) lies in a range of 0.03 to 0.1 mm$^2$.

3. Cylinder-piston unit according to claim 1, wherein the short cannula (61) has, at the front, a single cut with a short bevel design in accordance with DIN 13097-4 of August 2009.

4. Cylinder-piston unit according to claim 1, wherein the elastomer disc (110), in the installation position (111), has a sealing area (117) for closing the outlet opening (71) of the short cannula (61), the effect of which sealing area is no longer present in the application position (112).

5. Cylinder-piston unit according to claim 1, wherein the elastomer disc (110) has an adhesive coating (121) on the end face (113) directed away from the bottom portion (33) of the cylinder (20), the adhesive elastomer disc (110) detachable from the short cannula (61) in the application position (112) after an injection of the injection solution (1).

\* \* \* \* \*